United States Patent [19]
Wagnon et al.

[11] Patent Number: 4,725,580
[45] Date of Patent: Feb. 16, 1988

[54] PEPTIDE DERIVATIVES, ANALOGOUS TO PEPSTATIN, WHICH INHIBIT RENIN AND ACID PROTEASES

[75] Inventors: Jean Wagnon; Georges Callet, both of Montpellier; Jean-Pierre Gagnol, Saint Martin de Londres; Dino Nisato, Saint-Georges d'Orques; Catherine Cazaubon, Montpellier, all of France

[73] Assignee: Sanofi, France

[21] Appl. No.: 826,349

[22] Filed: Feb. 5, 1986

[30] Foreign Application Priority Data

Feb. 12, 1985 [FR] France ............................. 85 01982
Feb. 12, 1985 [FR] France ............................. 85 01981

[51] Int. Cl.⁴ .................... A61K 37/43; C07K 7/06
[52] U.S. Cl. ..................................... 514/17; 530/330; 530/332
[58] Field of Search ................... 514/17; 530/330, 332

[56] References Cited

FOREIGN PATENT DOCUMENTS 0081783 6/1983 European Pat. Off. .
2531951 2/1984 France .

*Primary Examiner*—Delbert R. Phillips
*Attorney, Agent, or Firm*—Bacon & Thomas

[57] ABSTRACT

The invention relates to pepstatin analogs which inhibit renin and acid proteases.

These analogs are particularly suitable for the treatment of arterial tension.

4 Claims, No Drawings

PEPTIDE DERIVATIVES, ANALOGOUS TO PEPSTATIN, WHICH INHIBIT RENIN AND ACID PROTEASES

The present invention relates to new peptide derivatives which inhibit renin and acid proteases. It also relates to a process for their preparation and their application in therapy.

In 1970, UMEZAWA isolated a pentapeptide from a culture of streptomyces; this pentapeptide was called pepstatin and its structure was subsequently established and corresponds to the formula:

isovaleryl-L-valyl-L-valyl-statyl-L-alanyl-statin in which the name "statin" denotes the uncommon amino acid (3S,4S)-4-amino-3-hydroxy-6-methylheptanoic acid.

It has been shown that pepstatin inhibits acid proteases and is active especially against pepsin, cathepsin D and renin. In particular, renin, an enzyme originating from the kidney, is involved in the sequence angiotensinogen—angiotensin I—angiotensin II in the conversion of angiotensinogen to angiotensin.

As a powerful vasoconstrictor, angiotensin II plays a part in regulating the arterial pressure. The possibility of using pepstatin to combat arterial hypertension in man has been considered. However, since pepstatin acts on all acid proteases and has a low solubility in aqueous media and a low affinity for renin, its use in therapy has proved difficult. Pepstatin derivatives have been described in the scientific literature. For example, attempts have been made to solubilize pepstatin by lengthening the peptide chain (J. Cardiovasc. Pharmacol., 1980, 2, 687–698).

By contrast, the present invention relates to peptides modeled on the basis of pepstatin. In certain cases, the introduction of unnatural amino acids makes it possible to increase the solubility of these compounds and their resistance to proteolysis. Totally surprisingly, it has been found that the peptides according to the invention, which carry hydrophilic residues at various sites, have a high level of activity which is greatly superior to that of pepstatin as an inhibitor of human renin.

The present invention relates to peptides having a high level of activity as inhibitors of renin and other acid proteases.

The following abbreviations will be used in the present description and in the claims:

AMINO ACIDS AND PROTECTING OR ACTIVATING GROUPS

These abbreviations are consistent with those indicated by the Nomenclature Commission of IUPAC-IUB, Biochemistry Section. The most recent recommendations are reported in Eur. J. Biochem., 1984, 138, 5–7 and 9–37.

Amino Acids and Derivatives

Ala: alanine
Asn: asparagine
Asp: aspartic acid
Gln: glutamine
Gly: glycine
His: histidine
Ile: isoleucine
Leu: leucine
Met: methionine
Nle: norleucine
Nva: norvaline
Phe: phenylalanine
Ser: serine
Sta: statin
AHPPA: 4-amino-3-hydroxy-5-phenylpentanoic acid
ACHPA: 4-amino-5-cyclohexyl-3-hydroxypentanoic acid
Met($O_2$): methionine dioxide
Abu: 2-aminobutyric acid Unless indicated otherwise, these amino acids have the L configuration.

Unless indicated otherwise, Sta, AHPPA and ACHPA have the 3S,4S configuration.

Protecting and Activating Groups

Ac: acetyl
Boc: t-butoxycarbonyl
$(Boc)_2O$: bis(tert.-butoxycarbonic)anhydride
HONSu: N-hydroxysuccinimide
OEt: ethyl ester
OMe: methyl ester
ONp: p-nitrophenyl ester
ONSu: N-hydroxysuccinimide ester
OTcp: 2,4,5-trichlorophenyl ester
iVa: isovaleryl
Z: benzoyloxycarbonyl The following abbreviations will also be used:
AcOEt: ethyl acetate
AcOH: acetic acid
Bop: benzyloxytrisdimethylaminophosphonium hexafluorophosphate
TLC: thin layer chromatography
DCCI: dicyclohexylcarbodiimide
DCHA: dicyclohexylamine
DCU: dicyclohexylurea
DIPEA: diisopropylethylamine
DMF: dimethylformamide
DMSO: dimethyl sulfoxide
Ether: ethyl ether
HOBt: 1-hydroxybenzotriazole
$KHSO_4$—$K_2SO_4$: aqueous solution containing 16.6 g of potassium bisulfate and 33.3 g of potassium sulfate per liter
MeOH: methanol
NEM: N-ethylmorpholine
NMM: N-methylmorpholine
RT: room temperature
TFA: trifluoroacetic acid
min: minutes
h: hours The compounds according to the invention correspond to the following general formula:

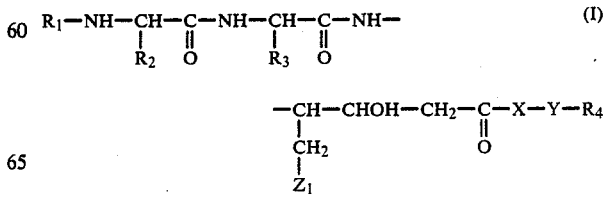

in which:

R₁ represents an acyl group chosen from the following groups: heterocyclylcarbonyl, heterocyclylalkylcarbonyl, in which the alkyl group is optionally substituted by a hydroxyl group, heterocyclylcarbonylalkylcarbonyl and heterocyclylalkenylcarbonyl, or represents a (lower alkyl)sulfonyl group which is unsubstituted or substituted on the alkyl by a free amino group or an amino group carrying a protecting group, or by a phenyl group, or represents a phenylsulfonyl group which is unsubstituted or substituted on the phenyl nucleus by a lower alkyl;

$R_2$ represents a lower alkyl group which is unsubstituted or substituted by a phenyl, naphthyl, cyclohexyl or pyridyl, or $R_2$ represents a phenyl, naphthyl, cyclohexyl or pyridyl radical;

$R_3$ represents a lower alkyl which is unsubstituted or substituted by a free amino group or an amino group carrying a protecting group, by a free carboxyl, by a hydroxyl group, by a lower alkylthio group, by a phenyl, by a naphthyl or by an imidazol-4-yl;

$R_4$ represents a hydroxyl, a lower alkoxy, a benzyloxy or a free amino group or an amino group substituted by one or 2 lower alkyls;

$Z_1$ represents isopropyl, phenyl or cyclohexyl, representively forming with the radical:

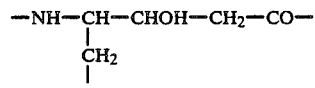

the residue of the amino acid statin, namely (3S,4S)-4-amino-3-hydroxy-6-methylheptanoic acid, of (3S,4S)-4-amino-3-hydroxy-5-phenylpentanoic acid (AHPPA) or of (3S,4S)-4-amino-5-cyclohexyl-3-hydroxypentanoic acid (ACHPA); and X—Y is a dipeptide chosen from the group comprising Ala-Sta, Ala-Leu, Leu-Phe, Val-Sta, Abu-Sta, Ile-Ser and Phg-Sta.

The present invention also includes any pharamceutically acceptable salts of the peptides of the formula (I) with mineral or organic acids or alkali metals or alkaline earth metals.

The term "alkyl" denotes saturated or unsaturated aliphatic hydrocarbon radicals containing 1 to 10 carbon atoms. The preferred "alkyl" groups for the purposes of the invention are the lower alkyl groups such as defined below.

The expressions "lower alkyl", "lower alkenyl" and "lower alkylidene", as used here, denote saturated or unsaturated aliphatic hydrocarbon radicals containing up to 6 carbon atoms.

The expressions "lower alkoxy" and "lower alkylthio" represent the hydroxyl and thiol groups substituted by a lower alkyl group such as defined above.

The expression "5-membered or 6-membered monocyclic heterocycle" includes pyrrolidine, imidazole, thiazole, thiophene, furan, pyrrole, triazole, oxazole, isoxazole, pyridine and thiadiazoles.

The expression "protecting group" is understood as meaning a protecting group normally used in peptide chemistry, for example Boc, Z or iVa.

The expression "acyl group" used to define $R_1$ includes the residues of heterocyclic carboxylic acids. Preferred acyl groups are the residue of a carboxylic acid in which the carboxyl is bonded to a 5-membered or 6-membered monocyclic heterocycle, especially the piperidinylcarboxyl groups, picolinoyl, nicotinoyl and isonicotinoyl groups, and the residue of alkanoic or alkenoic acids, such as acetic acid, propionic acid, butyric acid, valeric acid and their omega-hydroxy or omega-oxo derivatives substituted in the omega position by a 5-membered or 6-membered monocyclic heterocycle, as exemplified above.

More particularly, the present invention relates preferentially to the peptide derivatives of the formula (I) in which $R_2$, $R_3$, $R_4$, X, Y and $Z_1$ are as defined above and $R_1$ represents one of the following groups:

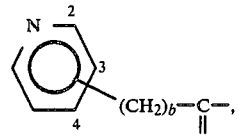

in which b = 0,1,2,3,4,5 or 6

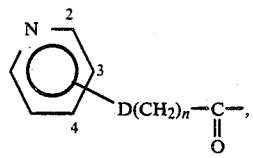

in which D = —CH— or —C—
              |           ||
              OH          O
and n = 1,2,3,4, or 5

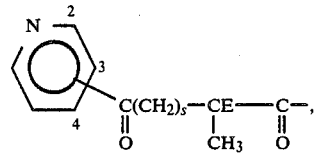

in which E = —H or —CH₃ and s = 1,2,3 or 4

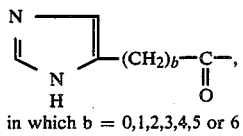

in which b = 0,1,2,3,4,5 or 6

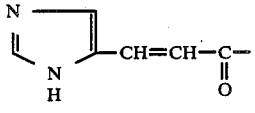

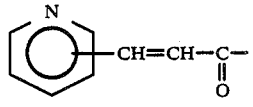

NH₂CH₂CH₂—SO₂—
BocNHCH₂CH₂—SO₂—
ZNHCH₂CH₂—SO₂—
A—SO₂—, in which A is a lower alkyl
C₆H₅—(CH₂)ₐ—SO₂—, in which a=0, 1 or 2

Particular preference is given to the peptide derivatives of the formula (I) in which $R_2$, $R_3$, $R_4$, X, Y and $Z_1$ are as defined above and $R_1$ represents an acyl group chosen from:
4-(pyridin-2-yl)-4-oxobutyryl,
4-(pyridin-2-yl)-4-hydroxybutyryl,
3-(pyridin-3-yl)propionyl,
4-(pyridin-3-yl)butyryl, nicotinoyl and
benzenesulfonyl.

The products according to the invention can be prepared by the methods normally used in peptide chemistry. More particularly, starting from a compound of the formula:

in which $R'_4$ is a lower alkoxy, a benzyloxy or a free amino group or an amino group substituted by one or two lower alkyls, and Y is chosen from the residues of the amino acids Sta, Leu, Phe and Ser, the various amino acids, appropriately protected, are coupled in a stepwise fashion, the product obtained at each step being deprotected by known processes before being subjected to further coupling, and each of the coupling operations being carried out using either an activated ester of the amino acid to be coupled or the N-protected amino acid in the presence of dicyclohexylcarbodiimide. The starting material is advantageously a lower alkyl ester of the C-terminal amino acid with which the next amino acid in the sequence is condensed. After the amine group of the dipeptide has been freed, the peptide chain is lengthened by coupling with the next, appropriately protected amino acid. Each coupling phase is followed by a selective operation to free the amine which will take part in the reaction to create the next peptide link. The various coupling operations are carried out either using an activated ester of the amino acid to be coupled or using the N-protected amino acid in the presence of dicyclohexylcarbodiimide. Depending on the nature of the protecting group used, the phases involving selective deprotection of the amine are carried out either by hydrogenolysis or by acidolysis in a strong acid medium such as trifluoroacetic acid. if the amino acid to be introduced into the sequence has a reactive group in its side chain, the said group should be blocked by an appropriate protecting group, which is subsequently removed.

The protection of the initial amino acid by the group $R_1$ is carried out by known methods before the residue:

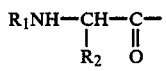

is coupled with the next amino acid.

The peptides (I) in the acid form ($R_4$=OH) can be obtained from the corresponding esters by saponification in a dilute alkaline medium. It is also possible to prepare their salts. The peptides (I) in the amide form ($R_4$=NH$_2$ or $R_4$=N(Alk)$_2$) are obtained directly by taking the commercially available amino acids in the amide form as the starting materials.

Any pharmaceutically acceptable salts of the peptides according to the invention with mineral or organic acids or alkali metals or alkaline earth metals are formed by conventional methods.

According to the general scheme, it is possible either to prepare the whole of the desired sequence or to prepare 2 fragments of this sequence, which are finally coupled to give the desired peptide.

The compounds of the present invention have a very strong inhibitory action on human plasma renin activity, which in general is considerably greater than that of the natural product: pepstatin; in this capacity, they can be used in the treatment of arterial hypertension.

They also possess a marked inhibitory action on acid proteases, especially pepsin. It is therefore possible to consider using the products according to the invention in areas of therapy where the inhibition of such enzyme systems is justified; apart from arterial hypertension, particularly relevant areas are gastroduodenal ulcers and inflammatory complaints.

The present invention also relates to antihypertensive pharmaceutical compositions in which the peptides of the formula (I) or their pharmaceutically acceptable salts are present as active principles.

The peptides of the present invention can be administered in therapy by intravenous, intramuscular or subcutaneous injection. They are used in a solvent such as physiological serum (isotonic saline solution) or in a buffer such as phosphate buffer; they can also be suspended in a pharmaceutically acceptable aqueous or non-aqueous diluent. Each dosage unit can contain from 1 to 1000 mg of active principle.

The quantity of active principle to be used varies according to the desired therapeutic effects, the severity of the complaint to be treated and the chosen method of administration. It must be determined for each patient and is most commonly between 0.100 g and 2 g of active principle.

The non-limiting examples which follow are given in order to illustrate the present invention.

In all these examples, the pH of the solutions in an organic solvent is measured or monitored using wet pH indicator paper.

The indicated melting points (m.p.) are measured by the capillary tube method.

Finally, the nuclear magnetic resonance spectra were run at 250 MHz in DMSO solution with hexamethyldisiloxane as the internal standard.

The following abbreviations are used:
s: singlet
d: doublet
m: multiplet or unresolved signals
q: quadruplet
Further abbreviations used are:
H ar denotes aromatic H
H im denotes H of the imidazole
H pyr denotes H of the pyridine The chemical shifts (delta) are measured in ppm.

EXAMPLE 1

N-(Nicotinoyl)-Phe-Nle-Sta-Ala-Leu-OMe (SR 42873)

1. Boc-Ala-Leu-OMe 2.86 g of Boc-Ala-ONSu, 1.81 g of Leu-OMe.HCl and 1.15 g of NEM are dissolved successively in 50 ml of CH$_2$Cl$_2$ at RT. The pH is checked to see that it is 6–7; if not, it is adjusted by the addition of NEM. The organic solution is stirred for 4 hours at RT and then washed successively with 5% KHSO$_4$—K$_2$SO$_4$ solution, water and 5% NaHCO$_3$ solution; it is dried over Na$_2$SO$_4$ and the solvent is then evaporated off to give an oil.

Yield: 2.93 g (92%).

2. Ala-Leu-OMe.TFA 360 mg of the previous product are covered with 5 ml of TFA. After 20 min, the TFA is evaporated off and the residue is taken up by a mixture of equal volumes of pentane and ether. A white solid appears on scratching and is filtered off, rinsed with ether and dried.

Yield: 320 mg (85%).

3. Boc-Sta-Ala-Leu-OMe 330 mg of the previously obtained TFA salt are solubilized in 30 ml of dioxane containing 230 mg of NEM; 275 mg of Boc-Sta-OH, 206 mg of DCCI and 135 mg of HOBt are added, the pH is adjusted to a value of 6–7 with NEM if necessary and the mixture is then stirred for 24 hours at RT. The DCU is filtered off, the solvent is evaporated off, the residue is dissolved in a mixture of equal volumes of AcOEt and hexane and the solution is chromatographed on a column of Merck 60 silica gel in the same solvent mixture, elution being carried out with 250 ml of the same solvent mixture, then 250 ml of the mixture in proportions of 75/25 by volume, and then 100 ml of AcOEt. The fractions containing the product are evaporated and the residues are taken up in ether, filtered off and dried.

Yield: 380 mg (80%).

4. Boc-Phe-Nle-Sta-Ala-Leu-OMe

This compound is prepared using the same coupling methods as above.

5. SR 42873

The product obtained in the previous step (200 mg) is placed in 3 ml of TFA at 0° C. for 10 min. The TFA salt obtained after the usual treatment is dissolved in 15 ml of $CH_2Cl_2$, the pH is brought to 7 by the addition of NMM, and 34 mg of nicotinic acid, 56 mg of DCCI and 42 mg of HOBt are added. After 24 hours, the mixture is treated in the usual way. The residue is chromatographed on silica by elution with AcOEt. This gives a homogeneous fraction of 45 mg.

| NMR SPECTRUM | | | |
| --- | --- | --- | --- |
| Delta | Appearance | Protons | Assignment |
| 7 and 8.95 | m | 14 H | 5 NH, 4 H pyr 5 H ar |
| 4.86 | d, J = 4 Hz | 1 H | 1 H, OH (Sta) |
| 4.25 | m | 3 H | H alpha (Phe, Nle, Leu) |
| 3.8 | s broad | 2 H | 2 H alpha (Sta, Ala) |
| 3.55 | s | 3 H | $OCH_3$ |

EXAMPLE 2

N-(4-Pyridin-2-yl)-4-oxobutyryl)-Phe-Nle-Sta-Leu-Phe-OMe (SR 42793)

1. N-(4-Pyridin-2-yl)-4-oxobutyryl)-Phe-OMe 1 g of Phe-OMe.HCl and 830 mg of (pyridin-2-yl)-4-oxobutyric acid are stirred in 10 ml of acetonitrile in the presence of 2.05 g of Bop and 940 mg of NEM. After 3 days, the mixture is evaporated to dryness, water and AcOEt are added and the mixture is washed several times with an aqueous solution of carbonate, water and an aqueous solution of sodium chloride, dried and evaporated. 1.25 g of a solid are isolated; this is purified by chromatography on silica gel, elution being carried out with a mixture of equal volumes of pentane and AcOEt. After recrystallization from a $CH_2Cl_2/Et_2O$ mixture, 870 mg of the expected product are obtained.

2. N-(4-(Pyridin-2-yl)-4-oxobutyryl)-Phe-OH 810 mg of the above ester in 15 ml of methanol are hydrolyzed for 4 hours at RT with 190 mg of sodium hydroxide in 5 ml of water. The mixture is evaporated to dryness, an aqueous solution of carbonate is added, extraction is carried out with AcOEt and the aqueous phase is then acidified to pH 4.65, monitoring with a pH meter. Extraction is then carried out with AcOEt and the extract is washed with water and an aqueous solution of sodium chloride and evaporated. The white solid obtained is recrystallized from an MeOH/$Et_2O$ mixture; m.p.=115°–120° C.

3. SR 42793

The previously described methods are then followed to give the expected product.

| NMR SPECTRUM | | | |
| --- | --- | --- | --- |
| Delta | Appearance | Protons | Assignment |
| 8.67–7.05 | m | 19 H | 5 NH CO 10 H ar $C_6H_5$, 4 H ar $C_5H_4N$ |
| 4.78 | d, J = 4 Hz | 1 H | OH (Sta) |
| 4.50–4.11 | m | 4 H | CH (alpha) |
| 3.81–3.67 | m | 2 H | CHOH (Sta) C$\underline{H}$NH (Sta) |
| 3.48 | s | 3 H | $OCH_3$ |
| 2.13–2.00 | m | 2 H | $CH_2CO$ (Sta) |
| 1.71–1.05 | m | 12 H | aliphatic CH, $CH_2$ |
| 0.89–0.68 | m | 15 H | $CH_3$ (Nle) $(CH_3)_2CH$ (Leu) $(CH_3)_2CH$ (Sta) |

EXAMPLE 3

(R,S)-N-(4-Pyridin-2-yl)-4-hydroxybutyryl)-Phe-Nle-Sta-Leu-Phe-OMe (SR 42991)

This compound is obtained by reducing SR 42793. 23 mg of SR 42793 are dissolved in 2 ml of MeOH, and 10 mg of $NaBH_4$ are added at RT. After 18 h, an excess of $KHSO_4$ solution is added, the mixture is stirred for 10 min, an aqueous solution of carbonate is then added and the MeOH is evaporated off in the cold. Extraction is carried out with 3 volumes of AcOEt and the extract is washed with water and dried over $K_2SO_4$. On evaporation, a solid is isolated which is triturated in an ether/hexane mixture to give 16 mg of the expected product.

| NMR SPECTRUM | | | |
| --- | --- | --- | --- |
| Delta | Appearance | Protons | Assignment |
| 8.43–7.0 | m | 19 H | 5 NH CO 10 H ar $C_6H_5$, 4 H ar $C_5H_4N$ |
| 5.34 | d, J = 4 Hz | 1 H | OH |
| 4.80 | d, J = 4 Hz | 1 H | OH (Sta) |
| 4.70–4.00 | m | 5 H | CH (alpha) |
| 3,80–3.66 | m | 2 H | CHOH (Sta) |
| 3.48 | s | 3 H | $OCH_3$ |
| 2.13–0.63 | m | 33 H | |

The following compounds were prepared using the same coupling methods:

| SR No. | Formula |
|---|---|
| 43108 | N—(4-(pyridin-3-yl)-4-oxobutyryl)-Phe—Nle—Sta—Leu—Phe—OMe |
| 43123 | (R,S)—N—(4-(pyridin-3-yl)-4-hydroxybutyryl)-Phe—Nle—Sta—Leu—Phe—OMe |
| 43282 | N—(pyridin-3-ylacetyl)-Phe—Nle—Sta—Leu—Phe—OMe |
| 43314 | N—(pyridin-2-ylacetyl)-Phe—Nle—Sta—Leu—Phe—OMe |
| 43454 | N—(3-(pyridin-3-yl)propionyl)-Phe—Nle—Sta—Leu—Phe—OMe |
| 43484 | N—(4-(pyridin-2-yl)butyryl)-Phe—Nle—Sta—Leu—Phe—OMe |
| 43519 | N—(N—Boc-piperidin-3-ylacetyl)-Phe—Nle—Sta—Leu—Phe—OMe |
| 43633 | N—(3-(pyridin-4-yl)propionyl)-Phe—Nle—Sta—Leu—Phe—OMe |
| 43781 | N—(pyridin-4-ylacetyl)-Phe—Nle—Sta—Leu—Phe—OMe |
| 43782 | N—(4-(pyridin-3-yl)butyryl)-Phe—Nle—Sta—Leu—Phe—OMe |

These products are characterized by their NMR spectrum.

| Delta | Appearance | Protons | Assignment |
|---|---|---|---|
| NMR SPECTRUM OF SR 43108 | | | |
| 9.02–7 | m | 19 H | 10 H C$_6$H$_5$, 4 H C$_5$H$_4$N, 5 NHCO |
| 4.80 | d, J = 4 Hz | 1 H | OH (Sta) |
| 4.52–4.09 | m | 4 H | CH (alpha) |
| 3.85–3.70 | m | 2 H | CHOH and C$\underline{H}$NH (Sta) |
| 3.48 | s | 3 H | OCH$_3$ |
| 2.12–2.00 | m | 2 H | CH$_2$CO (Sta) |
| 1.70–1.08 | m | 12 H | aliphatic CH and CH$_2$ (Nle, Leu, Sta) |
| 0.92–0.71 | m | 15 H | CH$_3$ (Nle, Leu, Sta) |
| NMR SPECTRUM OF SR 43123 | | | |
| 8.43–7.00 | m | 19 H | 10 H C$_6$H$_5$, 4 H C$_5$H$_4$N, 5 H NHCO |
| 5.33 | d, J = 4 Hz | 1 H | OH |
| 4.83 | d, J = 4 Hz | 1 H | OH (Sta) |
| 4.72–3.70 | m | 7 H | CH (alpha) CHOH (Sta) C$\underline{H}$NH (Sta) |
| 3,50 | s | 3 H | OCH$_3$ |
| 2.15–0.70 | m | 33 H | |
| NMR SPECTRUM OF SR 43282 | | | |
| 8.41–7.02 | m | 19 H | C$_6$H$_5$, C$_5$H$_4$N, NHCO |
| 4.85 | d, J = 4 Hz | 1 H | OH |
| 4.61–4.12 | m | 4 H | CH alpha |
| 3.84–3.68 | m | 2 H | CHNH and CHOH (Sta) |
| 3.49 | s | 3 H | OCH$_3$ |
| 3.45–3.18 | m | | CH$_2$C$_5$H$_4$N (+H$_2$O from DMSO) |
| 3.02–2.61 | m | 4 H | C$\underline{H}_2$C$_6$H$_5$ |
| 2.13–2.0 | m | 2 H | C$\underline{H}_2$CO (Sta) |
| 1.68–1.04 | m | 12 H | CH$_2$ (Nle); CH and CH$_2$ (Sta and Leu) |
| 0.85–0.66 | m | 15 H | CH$_3$ (Nle, Sta, Leu) |
| NMR SPECTRUM OF SR 43314 | | | |
| 8.42–7.02 | m | 19 H | C$_6$H$_5$, C$_5$H$_4$N, NHCO |
| 4.82 | d, J = 4 Hz | 1 H | OH |
| 4.60–4.14 | m | 4 H | CH alpha |
| 3.85–3.70 | m | 2 H | CHNH and CHOH (Sta) |
| 3.53 | s | 2 H | C$\underline{H}_2$C$_5$H$_4$N |
| 3.49 | s | 3 H | OCH$_3$ |
| 3.04–2.63 | m | 4 H | C$\underline{H}_2$C$_6$H$_5$ |
| 2.11–2.00 | m | 2 H | C$\underline{H}_2$CO (Sta) |
| 1.72–1.08 | m | 12 H | CH$_2$ (Nle); CH and CH$_2$ (Sta and Leu) |
| 0.82–0.64 | m | 15 H | CH$_3$ (Nle, Sta, Leu) |
| NMR SPECTRUM OF SR 43454 | | | |
| 8.36–7.075 | m | 19 H | C$_5$H$_4$N, C$_6$H$_5$, NHCO |
| 4.84 | d, J = 4 Hz | 1 H | OH |
| 4.57–4.12 | m | 4 H | CH alpha (Phe, Leu, Nle) |
| 3.84–3.67 | m | 2 H | CHNH, CHOH (Sta) |
| 3.49 | s | 3 H | OCH$_3$ |
| 3.03–2.57 | m | 6 H | C$\underline{H}_2$C$_6$H$_5$, C$\underline{H}_2$C$_5$H$_4$N |
| 2.31 | t, J about 6 Hz | 2 H | —C$\underline{H}_2$—CH$_2$—CO |
| 2.13–2.03 | m | 2 H | CH$_2$CO (Sta) |
| 1.70–1.09 | m | 12 H | CH$_2$ (Nle), CH, CH$_2$ (Leu), CH, CH$_2$ (Sta) |
| 0.85–0.66 | m | 15 H | CH$_3$ |
| NMR SPECTRUM OF SR 43484 | | | |
| 8.54–7.04 | m | 19 H | H ar, NHCO |
| 4.87 | d, J = 4 Hz | 1 H | OH |
| 4.61–4.14 | m | 4 H | CH alpha (Phe, Nle—Leu) |
| 3.87–3.70 | m | 2 H | CHNH, CHOH (Sta) |
| 3.50 | s | 3 H | OCH$_3$ |
| 3.04–2.62 | m | 4 H | C$\underline{H}_2$C$_6$H$_5$ |
| 2.62–2.41 | m | | C$\underline{H}_2$C$_5$H$_4$N (+DMSO) |
| 2.14–1.95 | m | 4 H | CH$_2$CO (Sta) C$_5$H$_4$N—CH$_2$CH$_2$—CH$_2$ |
| 1.78–1.10 | m | 14 H | C$_5$H$_4$N—CH$_2$—CH$_2$—CH$_2$, CH$_2$ (Nle) CH, CH$_2$ (Sta, Leu) |
| 0.91–0.67 | m | 15 H | CH$_3$ |
| NMR SPECTRUM OF SR 43633 | | | |
| 8.37–8.15 | m | 3 H | 2 H ortho C$_5$H$_4$N, NHCO |
| 8.18–8.03 | m | 2 H | NHCO |
| 7.75 | d, J = 8 Hz | 1 H | NHCO |
| 7.37 | d, J = 8 Hz | 1 H | NHCO (Sta) |
| 7.27–7.00 | m | 10 H 2 H | C$_6$H$_5$ C$_5$H$_4$N |
| 4.84 | d, J = 4 Hz | 1 H | OH (Sta) |
| 4.59–4.13 | m | 4 H | CH alpha (Phe, Nle, Leu) |
| 3.87–3.68 | m | 2 H | CHNH and CHOH (Sta) |
| 3.50 | s | 3 H | OCH$_3$ |
| 3.00–2.58 | m | 6 H | C$\underline{H}_2$C$_6$H$_5$ C$\underline{H}_2$C$_5$H$_4$N |
| 2.38–2.00 | m | 4 H | C$\underline{H}_2$—CH$_2$—CO CH$_2$CO (Sta) |
| 1.71–0.61 | m | 27 H | CH, CH$_2$, CH$_3$ (Nle, Leu, Sta) |
| NMR SPECTRUM OF SR 43782 | | | |
| 8.37–8.23 | m | 3 H | 2 H ortho C$_5$H$_4$N, NHCO |
| 8.10–7.97 | 2 d, J = 8 Hz | 2 H | NHCO |
| 7.73 | d, J = 8 Hz | 1 H | NHCO |
| 7.50–7.05 | m | 10 H 2 H 1 H | C$_6$H$_5$ C$_5$H$_4$N NHCO |
| 4.80 | d, J = 4 Hz | 1 H | OH (Sta) |
| 4.60–4.15 | m | 4 H | CH alpha (Phe, Nle, Leu) |
| 3.80–3.70 | m | 2 H | CHNH and C$\underline{H}$OH (Sta) |
| 3.49 | s | 3 H | OC$\underline{H}_3$ |
| 3.05–2.6 | m | 4 H | C$\underline{H}_2$C$_6$H$_5$ |

-continued

| Delta | Appearance | Protons | Assignment |
|---|---|---|---|
| 2.40–1.92 | m | 6 H | $C_5H_4NCH_2$ $CH_2$—CO (Sta) —$CH_2$—$CH_2$—$CH_2CO$ |
| 1.70–0.6 | m | 29 H | —$CH_2CH_2CH_2$—CO and CH, $CH_2$, $CH_3$ (Leu, Nle, Sta) |

The products according to the invention were studied for their therapeutic properties and especially their inhibitory action on enzymes. More particularly, the compounds were evaluated "in vitro" in terms of their inhibition of human plasma renin activity (PRA).

I—METHOD

The method of evaluation is based on that of GUYENE (J. Clin. Endocrinol. Metab., 1976, 43, 1301) to the extent that the inhibition of PRA is evaluated from a human plasma pool rich in renin (15 to 20 mg of angiotensin I released per milliliter and per hour), incubated for 60 minutes at 37° C., in a phosphate buffer at pH 7.4, in the presence of increasing concentrations of the product to be studied.

Human plasma contains the substrate angiotensinogen and the enzyme renin. The angiotensin I released during the reaction is measured by radioimmunoassay using a kit: Plasma Renin Activity Kit from Travenol (No. CA 533553). An inhibitor of the conversion enzyme, phenylmethylsulfonyl fluoride (PMSF), is added to the incubation medium. The total incubation volume is 555 microliters divided up as follows:
420 microliters of human plasma
11 to 50 microliters of the product to be studied, at variable concentrations
119 to 80 microliters of phosphate buffer
5 microliters of PMSF.

A solution of acetic acid in methaol (19/1 by volume) and a solution of sodium hydroxide in methanol (2/1 by volume) are prepared. In a mixture of equal volumes of these 2 solutions, a 0.001M stock solution of the peptide is prepared. The subsequent dilutions of the peptide are then made up in the phosphate buffer.

The quantity of solvent present in a solution of the peptide at a concentration of less than 0.0001M does not interfere with the results.

II—RESULTS

The results are expressed as the dose of compound, evaluated in mol, which causes a 50% inhibition ($IC_{50}$) of the human plasma renin activity observed in the absence of inhibitor.

The results obtained with various products of the invention are given in the following Table (I), which shows the $IC_{50}$ values of each molecule in terms of their inhibition of human plasma renin activity at pH 7.4. From 5 to 10 doses were required in order to determine these $IC_{50}$ values. Pepstatin, used as the reference substance, is always tested in parallel in each experiment. The results are expressed by their logarithmic value ($-\log IC_{50}$).

TABLE I

| SR No. | Inhibition of human PRA $-\log IC_{50}$ M pH 7.4 |
|---|---|
| Pepstatin | 4.92 |
| 42793 | 6.05 |
| 42873 | 7.09 |
| 42991 | 7.23 |
| 43108 | 6.35 |
| 43123 | 7.09 |
| 43282 | 7.10 |
| 43314 | 6.53 |
| 43454 | 7.17 |
| 43484 | 7.00 |
| 43519 | 6.76 |
| 43633 | 6.69 |
| 43781 | 6.88 |
| 43782 | 7.38 |

The toxicity of the products according to the invention is compatible with their use in therapy.

What is claimed is:

1. A peptide derivative of the formula:

$$R_1-NH-CH-C-NH-CH-C-NH- \quad (I)$$
$$\qquad\quad |\quad \|\qquad\quad |\quad \|$$
$$\qquad\quad R_2\ \ O\qquad\quad R_3\ \ O$$

$$-CH-CHOH-CH_2-C-X-Y-R_4$$
$$|\qquad\qquad\qquad\qquad\ \|$$
$$CH_2\qquad\qquad\qquad\ O$$
$$|$$
$$Z_1$$

in which:

$R_1$ represents:

[pyridyl ring structure]—$(CH_2)_b$—C(=O)— where b is 0,1,2,3,4,5 or 6;

[pyridyl ring structure]—D—$(CH_2)_n$—C(=O), where D is —CH— or —C— and n is 1,2,3,4 or 5;
         |          ‖
         OH         O

[pyridyl ring structure]—C(=O)—$(CH_2)_s$—CE—C(=O)—
                                        |
                                        $CH_3$ where E is —H or —$CH_3$ and s is 1,2,3 or 4; or

[piperidyl ring with W–N]—$(CH_2)_b$—C(=O)— where b = 0,1,2,3,4,5,6 and W is H or Boc;

$R_2$ represents benzyl;
$R_3$ represents a lower alkyl or a 4-imidazolyl;
$R_4$ represents a hydroxyl, a lower alkoxy, a benzyloxy or a free amino group or an amino group substituted by one or 2 lower alkyls;

$Z_1$ represents isopropyl, phenyl or cyclohexyl, respectively forming with the radical:

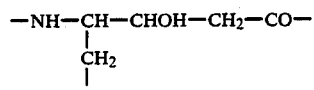

the residue of the amino acid statin, namely (3S,4S)-4-amino-3-hydroxy-6-methylheptanoic acid, of 3S,4S)-amino-3-hydroxy-5-phenylpentanoic acid (AHPPA) or of (3S,4S)-4-amino-5-cyclohexyl-3-hydroxypentanoic acid (ACHPA); and X—Y is a dipeptide selected from the group consisting of Ala-Sta, Ala-Leu, Leu-Phe, and Val-Sta; or a pharmaceutically acceptable salt thereof with mineral or orgaic acids or with alkali metals or alkaline earth metals.

2. A peptide derivative as claimed in claim 1 wherein $R_1$ is 4-(pyridin-2-yl)-4-oxbutyryl, 4(pyridin-2-yl)-4-hydroxybutyryl, 3-(pyridin-3-yl)propionyl, or 4-(pyridin-3-yl)butyryl.

3. A pharmaceutical composition for the treatment of arterial tension which contains an effective amount for the treatment of arterial tension of a product as claimed in claim 1 mixed with a pharmaceutical excipient.

4. A pharmaceutical composition as claimed in claim 2 in dosage unit form, which dosage unit contains from 1 to 1,000 mg of active ingredient.

* * * * *